US012797060B2

(12) United States Patent
Apsingi

(10) Patent No.: US 12,797,060 B2
(45) Date of Patent: Nov. 17, 2026

(54) CORTICAL BUTTON FOR SURGICAL FIXATION AND A SURGICAL FIXATION DEVICE THEREOF

(71) Applicant: HEALTHIUM MEDTECH LIMITED, Bengaluru (IN)

(72) Inventor: Sunil Apsingi, Nallakunta (IN)

(73) Assignee: Healthium Medtech Limited, Bengaluru (IN)

( * ) Notice: Subject to any disclaimer, the term of this patent is extended or adjusted under 35 U.S.C. 154(b) by 0 days.

(21) Appl. No.: 18/382,629

(22) Filed: Oct. 23, 2023

(65) Prior Publication Data

US 2025/0017582 A1 Jan. 16, 2025

(30) Foreign Application Priority Data

Jul. 13, 2023 (IN) ............................ 202341047187

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/0404* (2013.01)

(58) Field of Classification Search
CPC ............ A61F 2002/0852; A61F 2/0811; A61F 2002/0882; A61F 2002/0817; A61F 2002/0829; A61B 17/0401; A61B 2017/0404; A61B 2017/0406; A61B 2017/0414; A61B 2017/0417; A61B 17/06166
See application file for complete search history.

(56) References Cited

U.S. PATENT DOCUMENTS

2023/0338018 A1* 10/2023 Hustedt .............. A61B 17/0401
2024/0081808 A1* 3/2024 Hosseini ............ A61B 17/0401

FOREIGN PATENT DOCUMENTS

WO WO-2021101724 A1 * 5/2021 ......... A61B 17/0401
WO WO-2022187614 A1 * 9/2022 ......... A61B 17/0401
WO WO-2024238634 A1 * 11/2024 ......... A61B 17/0401

* cited by examiner

*Primary Examiner* — Katherine M Shi
(74) *Attorney, Agent, or Firm* — Foley & Lardner LLP

(57) ABSTRACT

The present disclosure discloses a cortical button for surgical fixation is disclosed. The cortical button includes a first section defining a substantially flat head and a second section defining a solid stub. The second section being co-axial to and extending substantially vertically from the first section. The first section being defined with a plurality of provisions. The plurality of provisions extending partially along an outer circumference of the second section and being configured to receive a suture.

13 Claims, 5 Drawing Sheets

A B

CORTICAL BUTTON FOR SURGICAL FIXATION AND A SURGICAL FIXATION DEVICE THEREOF

CROSS-REFERENCE TO RELATED PATENT APPLICATIONS

This application claims priority to and the benefit of the Indian Patent Application No. 202341047187, filed Jul. 13, 2023, the content of which is incorporated herein by reference in its entirety.

TECHNICAL FIELD

The present disclosure generally relates to the field of medical devices. Particularly but not exclusively, the present disclosure relates to a surgical fixation device. Further embodiments of the present disclosure disclose a cortical button for surgical fixation.

BACKGROUND

Joint injuries may commonly result in the complete or partial detachment of ligaments, tendons, and soft tissues from the bone. Tissue detachment may occur in many ways, e.g., as a result of an accident such as a fall, overexertion during a work-related activity, during the course of an athletic event, or in any one of many other situations and/or activities. These types of injuries are generally the result of excess stress or extraordinary forces being placed upon the tissues.

Repairing and reconstructing damaged tissues is a common practice in medical field. One such conventionally known method is using replacement graft ligaments. There are several known arts different ways of securing the replacement graft ligaments at site of original ligament within the tunnel formed in bone. One way is to insert interference screws parallel to the tunnel axis to compress the ends of the graft ligament against the wall of the bone tunnel to secure the graft ligament and promote tissue in-growth. These screws however can be non-adjustable and thus result in additional discomfort to the bones and tissues. There also are provisions for suspensory graft fixation devices which work with the help of a suture loop which supports one end of a graft ligament passed through the loop. However, in many instances, the loops are not adjustable or cannot be adjusted after they are locked in place.

SUMMARY

The shortcomings of the conventional art are overcome, and additional advantages are provided through the provision of device and system as disclosed in the present disclosure.

Additional features and advantages are realized through the techniques of the present disclosure. Other embodiments and aspects of the disclosure are described in detail herein and are considered a part of the disclosure.

In one non-limiting embodiment of the disclosure, a cortical button for surgical fixation is disclosed. The cortical button includes a first section defining a substantially flat head and a second section defining a solid stub. The second section being co-axial to and extending substantially vertically from the first section. The first section being defined with a plurality of provisions. The plurality of provisions extending partially along an outer circumference of the second section and being configured to receive a suture.

In an embodiment of the disclosure, the plurality of provisions is defined about a first imaginary axis and a secondary imaginary axis extending longitudinally along the outer circumference of the second section. The first imaginary axis and the second imaginary axis are separated by a distance equal to diameter of the second section. Each of the plurality of provisions is an aperture and the aperture is adapted to adjustably accommodate the suture.

In an embodiment of the disclosure, each of the plurality of provisions is a slotted aperture with a slot extending inwardly from a circumferential surface of the first section to an aperture defined about the first imaginary axis and the second imaginary axis.

In an embodiment of the disclosure, the first section and the second section are composed of magnetic resonance imaging compatible material including polyether-ether-ketone (PEEK).

In an embodiment of the disclosure, the first section is defined with a pre-determined thickness ranging from about 1.2 mm to about 1.7 mm. The second section is defined with a pre-determined height ranging from about 5.8 mm to about 6.3 mm.

In an embodiment of the disclosure, the diameter of the second section ranges from about 7.1 mm to about 7.9 mm.

In an embodiment of the disclosure, the diameter first section ranges from about 15.8 mm to about 16.2 mm. The diameter of the plurality of provisions ranges from about 1.72 mm to about 1.75 mm.

In an embodiment of the disclosure, a circumferential surface of the first section is chamfered. The chamfered radius ranges from about 0.2 mm to about 0.3 mm.

In an embodiment of the disclosure, the first section is defined with a cavity defined at a substantially central portion, the cavity extends up to a depth ranging from about 1.8 mm to about 2.2 mm.

In another non-limiting embodiment of the present disclosure, a surgical fixation device is disclosed. The surgical fixation device includes a cortical button configured to be ingressed into a tunnel defined in a bone. The cortical button includes a first section defining a substantially flat head and a second section defining a solid stub. The second section being co-axial to and extending substantially vertically from the first section. The first section being defined with a plurality of provisions. The plurality of provisions extending partially along an outer circumference of the second section. A suture is adjustably accommodatable in the plurality of provisions defined in the cortical button and being configured to secure and handle the tendon and to apply tension to the graft.

The foregoing summary is illustrative only and is not intended to be in any way limiting. In addition to the illustrative aspects, embodiments, and features described above, further aspects, embodiments, and features will become apparent by reference to the drawings and the following description.

BRIEF DESCRIPTION OF THE ACCOMPANYING FIGURES

The novel features and characteristic of the disclosure are set forth in the appended claims. The disclosure itself, however, as well as a preferred mode of use, further objectives, and advantages thereof, will best be understood by reference to the following detailed description of an illustrative embodiment when read in conjunction with the accompanying figures. One or more embodiments are now described, by way of example only, with reference to the accompanying figures wherein like reference numerals represent like elements and in which:

FIG. 1*a* illustrates schematic view of a surgical fixation device implanted in bone, in accordance with an embodiment of the disclosure.

FIG. 1*b* illustrates a perspective view of the surgical fixation device of FIG. 1*a*, in accordance with an embodiment of the present disclosure.

Figure 1A:
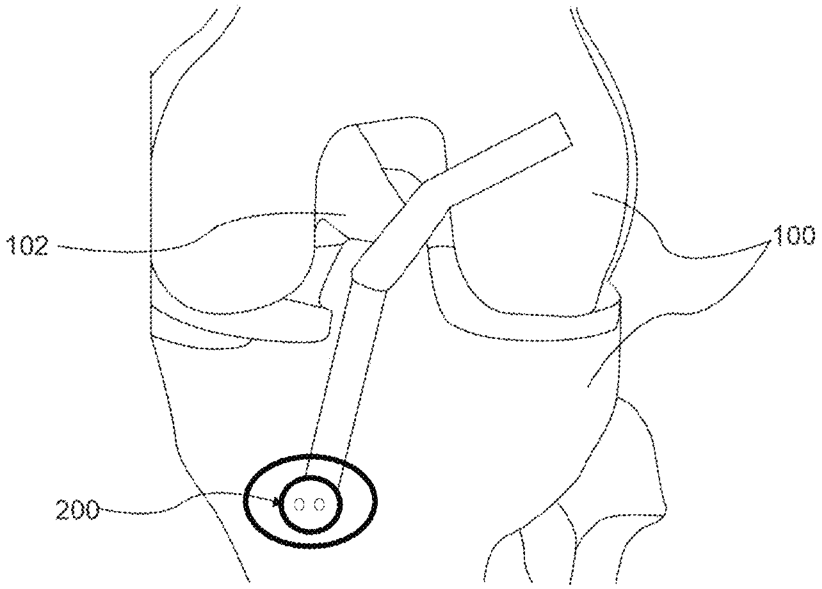

The figures depict embodiments of the disclosure for purposes of illustration only. One skilled in the art will readily recognize from the following description that alternative embodiments of the device and system illustrated herein may be employed without departing from the principles of the disclosure described herein.

DETAILED DESCRIPTION

The foregoing has broadly outlined the features and technical advantages of the present disclosure in order that the detailed description of the disclosure that follows may be better understood. Additional features and advantages of the disclosure will be described hereinafter which form the subject of the claims of the disclosure.

It should be appreciated by those skilled in the art that the conception and specific embodiments disclosed may be readily utilized as a basis for modifying or designing other systems for carrying out the same purposes of the present disclosure. It should also be realized by those skilled in the art that such equivalent processes do not depart from the scope of the disclosure as set forth in the appended claims. The novel features which are believed to be characteristics of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Embodiments of the present disclosure describes about a surgical fixation device suitable for use in anterior cruciate ligament (ACL) surgery and posterior cruciate ligament (PCL). The surgical fixation device in forthcoming embodiments may also be referred to as a suspensory fixation device without deviating from the scope of the present disclosure. The surgical fixation device may include a cortical button being adapted to be sit on the cortical bone and be ingressed into a tunnel defined in a bone. The cortical button may be defined with a first section defining a substantially flat head and a second section defining a solid stub. The second section may be coaxial to and may extend substantially vertically from the first section. The said first section being defined with a plurality of provisions. In an embodiment, each of the plurality of provisions may extend partially along an outer circumference of the second section. The plurality of provisions may be configured to receive a suture. The suture may be adjustably accommodatable in the plurality of provisions in the cortical button and may be adapted to secure and handle tendon. The said suture may be configured to apply tension to the graft. The surgical fixation device and the cortical button for the surgical fixation device will be elucidated comprehensively in conjunction with corresponding figures.

The terms "comprises . . . a", "comprising", or any other variations thereof used in the specification, are intended to cover a non-exclusive inclusion, such that an assembly that comprises a list of components or steps does not include only those components or steps but may include other components or steps not expressly listed or inherent to such setup or method. In other words, one or more elements in an assembly proceeded by "comprises . . . a" does not, without more constraints, preclude the existence of other elements or additional elements in the assembly. Henceforth, the present disclosure is explained with the help of one or more figures of exemplary embodiments. However, such exemplary embodiments should not be construed as limitation of the present disclosure.

The following paragraphs describe the present disclosure with reference to FIGS. 1*a* to 6. In the figures, the same element or elements which have similar functions are indicated by the same reference signs. The system described herein relates to a surgical fixation device generally identified by reference numeral 500 in the corresponding figures. Furthermore, the present disclosure may also describe a cortical button depicted by reference numeral 200 and 300 for use in the surgical fixation device (500). The surgical fixation device may also be referred to as a suspensory fixation device and is alternatively used henceforth.

The surgical fixation device in the present disclosure refers to a device that may be inserted surgically to keep bones stabilized or reconstruct the ligament in one or more locations in subjects body. The surgical fixation device (500) may be used in surgeries including but not limiting to anterior cruciate ligament (ACL) and posterior cruciate ligament (PCL). ACL in the specimens may generally connect the tibia to the femur i.e., the shin bone to the thigh bone. A tear in this ligament may cause specimens knee to swell, may feel unstable and may give away making the person stumble or fall. Surgery may be performed to reconstruct the ligament using minimal invasive arthroscopic technique which is referred to as the ACL reconstruction (ACLR). The surgical fixation device (500) of the present disclosure may be used for ACLR to repair or reconstruct the ligament i.e., a soft-tissue structure connecting the femur to the tibia. Similar to the ACLR, the PCLR may also employ the surgical fixation device (500) of the present disclosure. Although, specific surgical techniques are mentioned in present disclosure, the same should not be construed as a limitation of the present disclosure as the surgical fixation device (500) and components thereof may be employed in any such surgical techniques which require such surgical fixation device (500).

For the purposes of promoting an understanding of the principles of the disclosure, reference will now be made to specific embodiments illustrated in the drawings and specific language will be used to describe the same. It will nevertheless be understood that no limitation of the scope of the disclosure is thereby intended, such alterations and further modifications in the illustrated system, device, and such further applications of the principles of the disclosure as illustrated therein being contemplated as would normally occur to one skilled in the art to which the invention pertains.

The following detailed description is merely exemplary in nature and is not intended to limit application and uses. Furthermore, there is no intention to be bound by any theory presented in the preceding background or summary or the following detailed description. It is to be understood that the disclosure may assume various alternative orientations and step sequences, except where expressly specified to the contrary. It is also to be understood that the specific devices or components illustrated in the attached drawings and described in the following specification are simply exemplary embodiments of the inventive concepts defined in the appended claims. Hence, specific dimensions or other physical characteristics relating to the embodiments that may be disclosed are not to be considered as limiting, unless the claims expressly state otherwise. Hereinafter, preferred embodiments of the present disclosure will be descried referring to the accompanying drawings. While some specific terms of “upper,” “lower,” “right,” or “left”, “vertical” or “horizontal” and other terms containing these specific terms and directed to a specific orientation of the system as shown in figures and the purpose of usage of these terms or words is merely to facilitate understanding of the present disclosure referring to the drawings. Accordingly, it should be noted that the meanings of these terms or words should not improperly limit the technical scope of the present disclosure.

FIG. 1*a* in the corresponding figure depicts an exemplary schematic view of a knee joint of a specimen subjected to ACLR surgery. As apparent from FIG. 1, the surgical fixation device (500) may be used for ligament repair or reconstruction between the femur and the tibia. In the figures, the bone is depicted by 100, however the femur and tibia are not explicitly shown. Upon confirming the ACL tear in specimen, the practitioner may initially harvest and prepare the ACL graft. The graft in general may be a patellar tendon or a hamstring autograft from the specimen’s own body, and an allograft from a cadaver donor graft. Once the graft is harvested, the practitioner may create a tibial tunnel i.e., a tunnel in the shin bone and a femoral tunnel in the thigh bone. The graft may then be passed through the tibial tunnel and the femoral tunnel defined in the respective bones and secured to the femoral side and tibial side. Although, the ACLR is elucidated hereinabove, the application of the surgical fixation device (500) should not be construed as being limited to ACLR. The surgical fixation device (500) may also be employed in PCLR and the like without deviating from the scope of the present disclosure. The ACLR, PCLR procedure may be performed using the surgical fixation device (500) of the present disclosure.

Figure 1B:
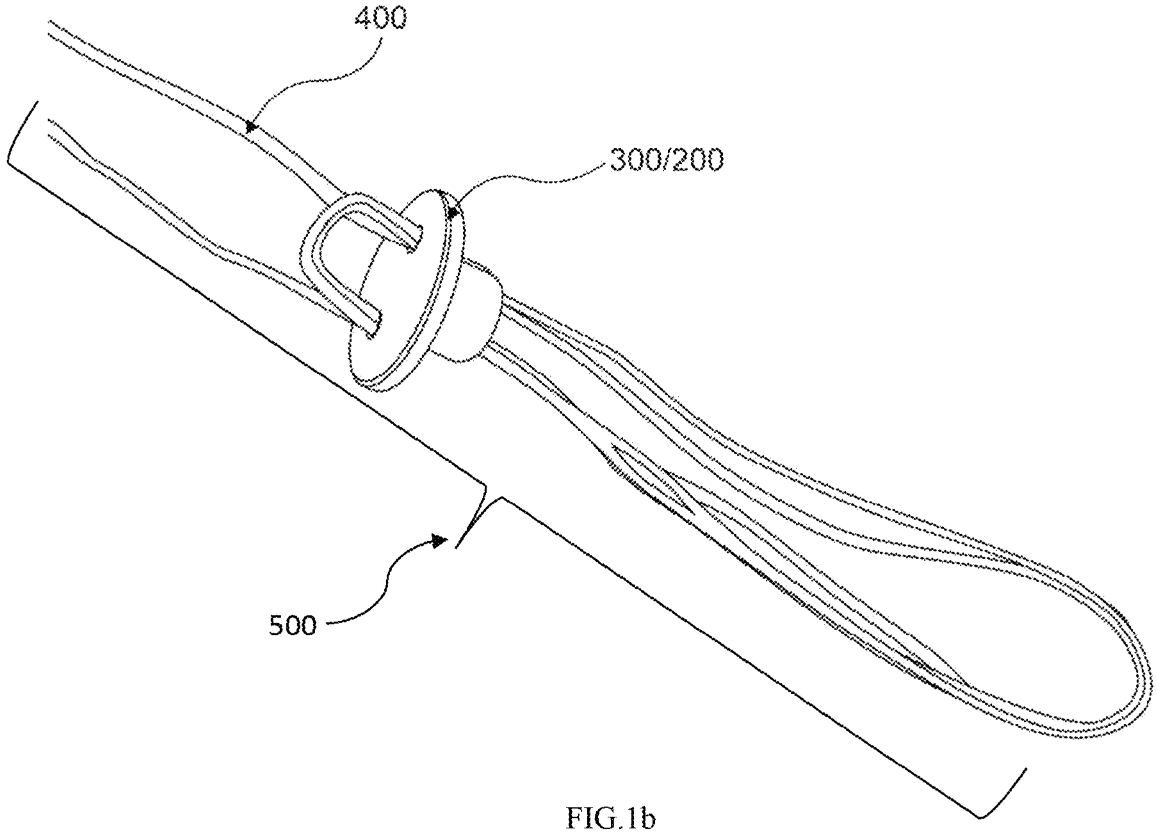
Figure 2:
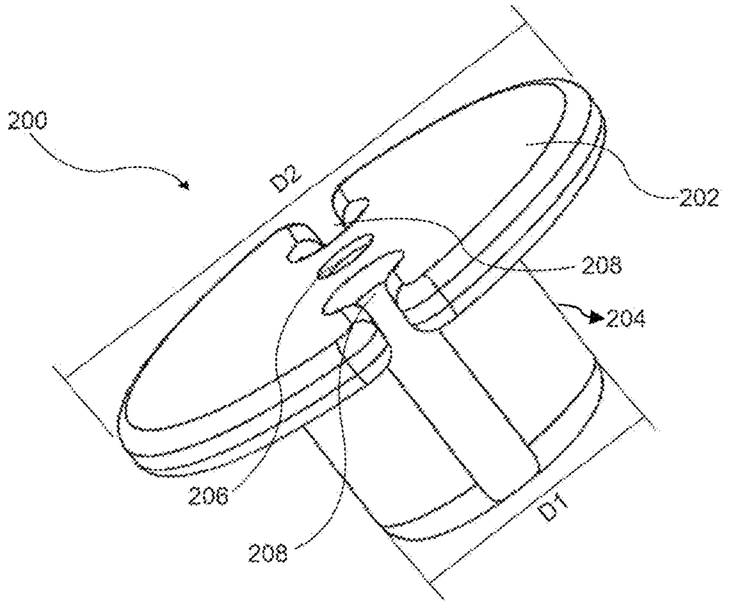
FIG. 2 illustrates perspective views of a cortical button in accordance with an embodiment of the disclosure.
Figure 3:
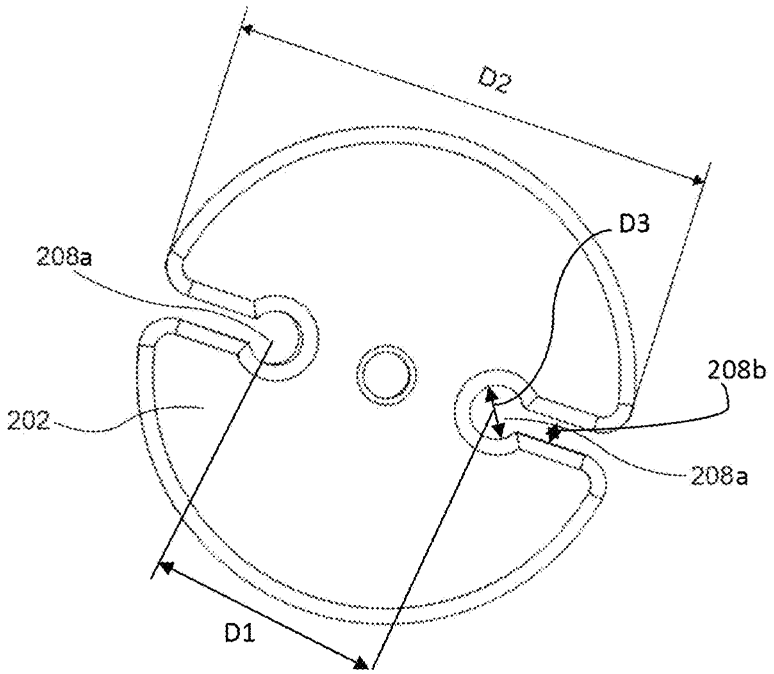
FIG. 3 illustrates top views of the cortical button of FIG. 2.
Figure 4:
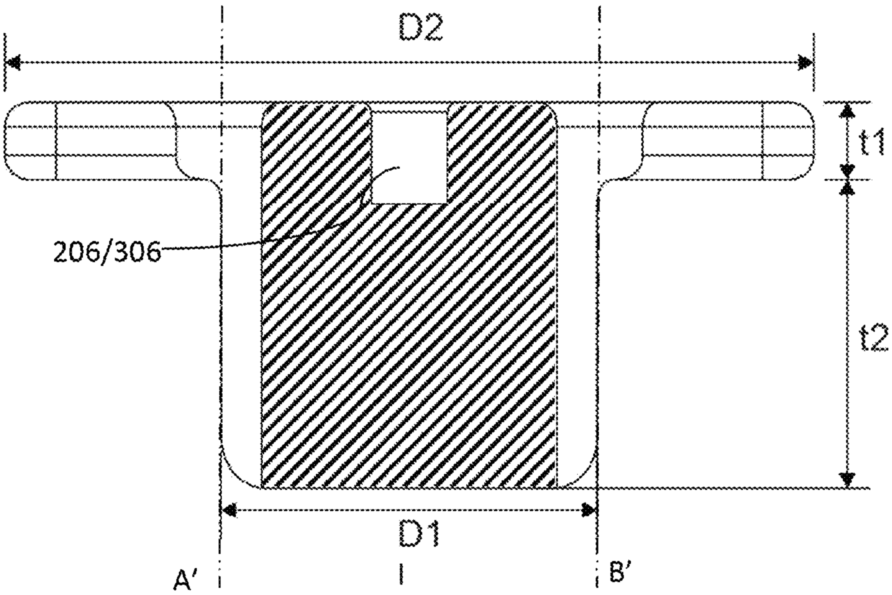
FIG. 4 illustrates a cross-sectional view of the cortical button of FIG. 2.
Figure 5:
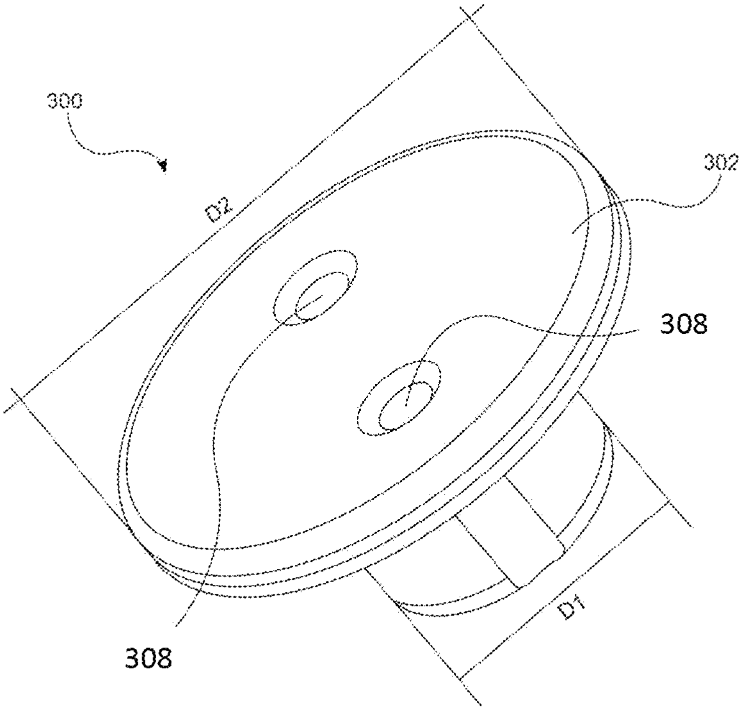
FIG. 5 illustrates perspective views of a cortical button in accordance with another embodiment of the disclosure.
Figure 6:
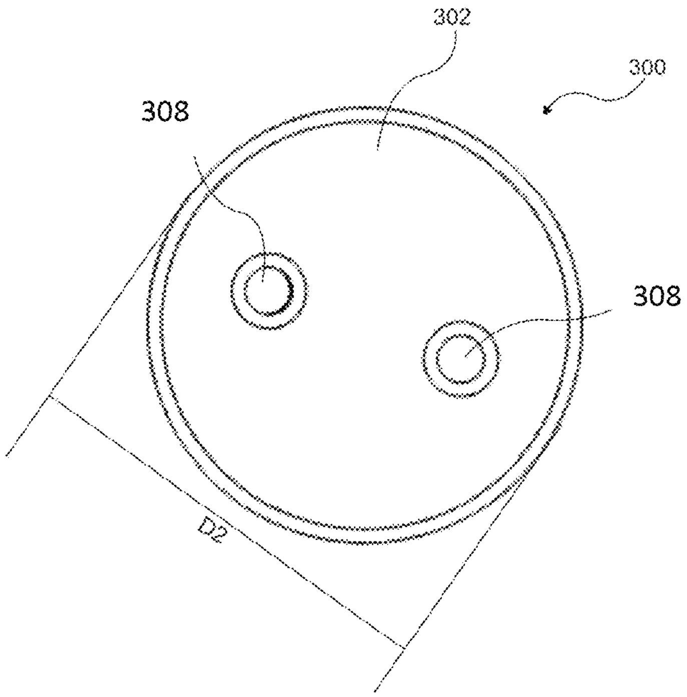
FIG. 6 illustrates a top view of the cortical button of FIG. 5.

As shown in FIG. 1*b*, the surgical fixation device (500) may include a suture (400) and a cortical button (200, 300). The suture (400) may be made of but not limiting a non-absorbable material including an ultra-high-molecular-weight polyethylene (UHMWPE, UHMW) or a high modulus polyethylene (HMPE). The suture (400) may be a strand used to pass the graft into the tibial and the femoral bone. Also, the suture (400) may be adapted to allow tensioning and adjustment of the loop’s length after graft may be inserted through the tibial tunnel and the femoral tunnel. The said suture (400) may be adjustably accommodatable in the cortical button (200, 300) of the surgical fixation device (500). The adjustably accommodatable suture (400) may ensure reduced bone removal, reduced femoral tunnel widening and improved graft healing. The suture (400) as described erst—while may be adjustably accommodatable in the cortical button (200, 300). In an embodiment, the cortical button (200, 300) may be composed of/made of a magnetic resonance imaging (MRI) compatible material or biocompatible material. The Cortical button (200, 300) may be made of non metallic material such as but not limiting to polyether-ether-ketone (PEEK). Henceforth, the cortical button (200, 300) may be elucidated in conjunction with FIGS. 2 to 6. FIGS. 2 and 5 in the corresponding figures illustrate a perspective view of the cortical button (200, 300) of the surgical fixation device (500). Likewise, FIGS. 3 and 6 in the figures illustrate a plan view or a top view of the cortical button (200, 300) of FIGS. 2 and 5, respectively. Further, FIG. 4 illustrates a cross-sectional view of the cortical button (200, 300) of FIGS. 2, 3, 5 and 6.

In the forthcoming paragraphs, the cortical button (200, 300) may be elucidated in conjunction with FIGS. 2 to 6, explicit reference will be made to corresponding figures wherever necessary. In an implementation, the cortical button (200, 300) may be a T-shaped member. The cortical button (200, 300) may be defined with a first section (202, 302). In an embodiment, the first section (202, 302) of the cortical button (200, 300) may be substantially circular when viewed in top view/plan view as apparent from FIGS. 3 and 6. The first section (202, 302) may be defined with a diameter (D2) ranging from about 15.8 mm to about 16.2 mm. In an embodiment, the first section (202, 302) may define a substantially flat head section as apparent from FIGS. 2 and 5. The flat headed first section (202, 302) may be defined with a thickness (t1) ranging from about 1.2 mm to about 1.7 mm. In an implementation, the circumferential surface of the first section (202, 302) may be chamfered or beveled. The radius of the chamfered circumferential surface of the first section (202, 302) ranges from about 0.2 mm to about 0.3 mm.

The cortical button (200, 300) may further include a second section (204, 304) defining a solid stub or a post. The said second section (204, 304) may extend substantially vertically from the first section (202, 302). The term of approximation such as “substantially” when used in reference to physical characteristics in the present disclosure, should be understood to contemplate a range of deviations that would be appreciated by one of ordinary skill in the art to operate satisfactorily for a corresponding use, function, purpose, or the like. The term “substantially” is a descriptive term commonly used in disclosures to avoid a strict numerical boundary to the specified parameter. The term “substantially” should be read in conjunction with the terms “perpendicular”, “central”, “circular”, “along a radius”, “vertical”, “conforming” etc. In an implementation, the second section (204, 304) may extend at a pre-defined angle from the first (202, 302). In an implementation, the second section (204, 304) may be coaxial to the first section (202, 302). That is the first section (202, 302) and the second section (204, 304) may be defined along a same axis (I-I) as apparent from FIG. 4. The second section (204, 304) may be substantially circular in cross-section and may be adapted to be received in the tunnel defined in the tibia and/or the femur i.e., the bone (100). The second section (204, 304) being solid may increase strength and rigidity of the cortical button (200, 300). The second section (204, 304) may be defined with a diameter (D1) ranging from about 7.1 mm to about 7.9 mm. Further, the second section (204, 304) may be defined with a height (t2) ranging from about 5.8 mm to about 6.3 mm. Although, the dimensions of the second section (204, 304) is illustrated in the present disclosure, the same should not be construed as a limitation of the present disclosure. The dimension of the second section (204, 304) may vary based on the type of such surgical techniques. Although specific dimensions of the first section (202, 302) and the second section (204, 304) is described, the same should not be construed as a limitation of the present disclosure. The dimensions of the cortical button (200, 300) may vary based on the type of ligament reconstruction without deviating from the scope of the present disclosure. In an implementation, a cavity (206, 306) may be defined in a substantially central portion of the first section (202, 302). The cavity (206, 306) may partially extend into the second section (204, 304) from the first section (202, 302). The cavity (206, 306) may extend up to a depth ranging from about 1.8 mm to about 2.2 mm from the surface of the first section (202, 302). In an implementation, the surface of the first section (202, 302) may be defined with a rougher surface aiding in better fixation of the cortical button (200, 300). In an implementation, the surface of the first section (202, 302) and the second section (204, 304) may be defined with a surface pattern. For instance, the surface of the first section (202, 302) and the second section (204, 304) may be knurled.

The first section (202, 302) of the cortical button (200, 300) may be defined with a plurality of provisions (208, 308). The said plurality of provisions (208, 308) may extend partially along an outer circumference of the second section (204, 304). The plurality of provisions (208, 308) may be defined as a first imaginary axis (A-A') and a second imaginary axis (B-B') extending longitudinally along the outer circumference of the second section (204). That is the first imaginary axis (A-A') and the second imaginary axis (B-B') may be defined vertically along the outer circumference of the second section (204, 304). In an implementation, the first imaginary axis (A-A') and the second imaginary axis (B-B') may be separated by a distance equal to a diameter (D1) of the second section (204, 304) i.e., about 7.1 mm to about 7.9 mm [refer FIG. 4]. In an embodiment, each of the plurality of provisions (208, 308) may be an aperture (308) as evident from FIGS. 5 and 6. The aperture (308) may be defined in the first section (302) about the first imaginary axis (A-A') and the second imaginary axis (B-B') with a diameter (D3). The diameter (D3) of the aperture (308) may range from about 1.72 mm to about 1.76 mm. The aperture (308) of the cortical button (300) may be configured to adjustably receive the suture (400). The aperture (308) of the cortical button (300) may define a closed variant of the cortical button (300) as apparent from FIGS. 5 and 6. The said aperture (308) may be extended beyond the first section (302) on to the outer circumference of the second section (304) along the first and the second imaginary axis (A-A' and B-B') as evident from FIG. 5. The aperture (308) extending beyond the first section (302) may define a groove along the outer circumference of the second section (304). The groove on the second section (304) may have common axis as that of the aperture (308). Each of the plurality of provisions (308) may adjustably receive the suture (400).

In another embodiment, each of the plurality of provisions (208, 308) may be a slotted aperture (208) as evident from FIGS. 2 and 4. The slotted aperture (208) may be defined in the first section (302) about the first imaginary axis (A-A') and the second imaginary axis (B-B'). the slotted aperture (208) may include an aperture (208*a*) and a slot (208*b*). The aperture (208*a*) may be defined in the first section (202) along the first imaginary axis (A-A') and the second imaginary axis (B-B'). The slot (208*b*) of the slotted aperture (208) may extend inwardly from the circumferential surface of the first section (202) to the aperture (208*a*). The diameter (D3) of the aperture (208*a*) may range from about 1.72 mm to about 1.76 mm and the width of the slot (208*b*) connecting the aperture (208*a*) may range from about 0.8 mm to about 1.0 mm. The suture (400) may be ingressed into the aperture (208*a*) through the slot (208*b*) of the cortical. The slotted aperture (208) of the cortical button (200) may define an open variant of the cortical button (200) as apparent from FIGS. 2 and 3. The said aperture (208) may be extended beyond the first section (202) on to the outer circumference of the second section (204) along the first and the second imaginary axis (A-A' and B-B') as evident from FIG. 4. The aperture (308) extending beyond the first section (202) may define a groove along the outer circumference of the second section (204). The groove on the second section (204) may have a common axis as that of the aperture (208*a*).

The surgical fixation device (500) of the present disclosure may provide a bio-mechanically higher graft durability, less bone tunnel widening. Further, the cortical button (200, 300) of the present disclosure being solid ensures durability, rigidity, and strength. Thereby, the cortical button (200, 300) of the present disclosure enables use of thicker graft for reconstruction. The configuration of the cortical button (200, 300) may ensure that the suture (400) may be adjustable after inserting into the bone tunnel. Also, the cortical button (200, 300) of the present disclosure provides a means for accurate suture fixation in the ligament reconstructive surgery.

It is to be understood that a person of ordinary skill in art may develop a similar system without deviating from the scope of the present disclosure. Such modifications and variations may be made without departing from the scope of the present invention. Therefore, it is intended that the present disclosure covers such modifications and variations provided they come within the ambit of the appended claims and their equivalents.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding the description, it may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated in the description.

What is claimed is:

1. A cortical button (200, 300) for surgical fixation, the cortical button (200, 300) comprising:
- a first section (202, 302) defining a substantially flat head; and
- a second section (204, 304) defining a solid stub, the second section (204, 304) being coaxial to and extending substantially vertically from the first section (202, 302),
- wherein, the first section (202, 302) being defined with a plurality of provisions (208, 308), the plurality of provisions (208, 308) extending partially along an outer circumference of the second section (204, 304) and being configured to receive a suture (400),
- wherein the first section is defined with a pre-determined thickness ranging from about 1.2 mm to about 1.7 mm.

2. The cortical button as claimed claim 1, wherein the plurality of provisions is defined about a first imaginary axis (A-A") and a second imaginary axis (B-B") extending longitudinally along the outer circumference of the second section, the first imaginary axis (A-A") and the second imaginary axis (B-B") is separated by a distance equal to a diameter (D1) of the second section.

3. The cortical button as claimed in claim 2, wherein each of the plurality of provisions is a slotted aperture comprising a slot extending inwardly from a circumferential surface of the first section to an aperture defined about the first imaginary axis (A-A") and the second imaginary axis (B-B").

4. The cortical button as claimed in claim 2, wherein each of the plurality of provisions is an aperture, the aperture is adapted to adjustably accommodate the suture.

5. The cortical button as claimed in claim 2, wherein each of the plurality of provisions is a slotted aperture comprising a slot extending inwardly from a circumferential surface of the first section to an aperture defined about the first imaginary axis (A-A") and the second imaginary axis (B-B").

6. The cortical button as claimed in claim 1, wherein each of the plurality of provisions is an aperture, the aperture is adapted to adjustably accommodate the suture.

7. The cortical button as claimed in claim 1, wherein the first section and the second section are composed of magnetic resonance imaging (MRI) compatible material including polyether-ether-ketone (PEEK).

8. The cortical button as claimed in claim 1, wherein the second section is defined with a pre-determined height ranging from about 5.8 mm to about 6.3 mm.

9. The cortical button as claimed in claim 1, wherein a diameter (D1) of the second section ranges from about 7.1 mm to about 7.9 mm.

10. The cortical button as claimed in claim 1, wherein a diameter (D2) of the first section ranges from about 15.8 mm to about 16.2 mm.

11. The cortical button as claimed in claim 1, wherein a diameter (D3) of the plurality of provisions ranges from about 1.72 mm to about 1.76 mm.

12. The cortical button as claimed in claim 1, wherein a circumferential surface of the first section is chamfered, wherein a radius of a chamfer ranges from about 0.2 mm to 0.3 mm.

13. The cortical button as claimed in claim 1, wherein the first section is defined with a cavity defined at a substantially central portion, the cavity extends up to a depth ranging from about 1.8 mm to about 2.2 mm.

* * * * *